United States Patent
Singh et al.

(10) Patent No.: US 10,071,403 B2
(45) Date of Patent: Sep. 11, 2018

(54) SYSTEM AND METHOD FOR DECOMPOSING MUNICIPAL SOLID WASTE (MSW) UNDER ANAEROBIC CONDITIONS

(71) Applicant: Indian Institute of Technology Bombay, Mumbai (IN)

(72) Inventors: Devendra Narain Singh, Mumbai (IN); Bhagawan Shamrao Patil, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 68 days.

(21) Appl. No.: 15/002,075

(22) Filed: Jan. 20, 2016

(65) Prior Publication Data
US 2017/0203344 A1    Jul. 20, 2017

(51) Int. Cl.
| | | |
|---|---|---|
| *B09B 1/00* | (2006.01) | |
| *B09B 3/00* | (2006.01) | |
| *C12M 1/107* | (2006.01) | |
| *C12M 1/16* | (2006.01) | |
| *C12M 1/00* | (2006.01) | |
| *C12M 1/34* | (2006.01) | |

(52) U.S. Cl.
CPC .................. *B09B 3/00* (2013.01); *B09B 1/00* (2013.01); *C12M 21/04* (2013.01); *C12M 21/16* (2013.01); *C12M 29/02* (2013.01); *C12M 41/12* (2013.01); *C12M 41/34* (2013.01)

(58) Field of Classification Search
CPC ......... B09B 3/00; C12M 29/02; C12M 41/00; C12M 41/12
USPC ......................................................... 435/262
See application file for complete search history.

(56) References Cited

U.S. PATENT DOCUMENTS 5,571,703 A * 11/1996 Chieffalo .................. B09B 3/00
426/11
2004/0191755 A1 * 9/2004 Kemper .................... B09B 1/00
435/3

* cited by examiner

*Primary Examiner* — Nathan A Bowers
*Assistant Examiner* — Lydia Edwards
(74) *Attorney, Agent, or Firm* — Rahman LLC

(57) ABSTRACT

A system and method for decomposing municipal solid waste (MSW) under anaerobic conditions. The system includes a bioreactor landfill with the MSW, a leachate recirculation unit in connection with the bioreactor landfill, a multilevel thermocouple unit, placed inside the bioreactor landfill for monitoring temperature in the bioreactor landfill. Further, the system includes a sensor for monitoring moisture level within the bioreactor landfill. Furthermore, the system includes the leachate recirculation unit configured to initiate recirculation of a leachate, collected from the bioreactor landfill, when temperature in the bioreactor reaches a determined temperature and a determined moisture level.

9 Claims, 7 Drawing Sheets

US 10,071,403 B2

SYSTEM AND METHOD FOR DECOMPOSING MUNICIPAL SOLID WASTE (MSW) UNDER ANAEROBIC CONDITIONS

TECHNICAL FIELD

The present invention relates to solid waste management, and more particularly relates to a system and method for decomposing Municipal Solid Waste (MSW) under anaerobic conditions.

BACKGROUND

Presently different types of the wastes are defined by the modern system of waste management are (namely, Municipal Solid Waste (MSW), construction and demolition waste, institutional, commercial, and industrial waste; medical wastes, hazardous wastes, radioactive wastes and electronic wastes). It is imperative to safely handle these wastes. Also, disposal of the MSW poses a great challenge to town planners and administrators.

Different methods for the disposal of MSW are composting (i.e., decomposition of the solid waste), incineration (i.e., burning of the waste in a furnace) and land-filling (i.e., burying the solid waste under various layers of the soil mass). The most preferred option of the MSW disposal is land-filling, where several layers of the soil mass are used for its stabilization (i.e., decomposition) with the help of natural metabolism (i.e., bacterial activity). Though, land-filling is one of the most attractive and economical paths adopted for the disposal of the MSW, as compared to other disposal methods, it necessitates acquisition of huge area of the land, optimization of the cost and various issues associated with the transportation of the MSW from different localities of the city to the landfill. In conventional systems, bioreactor landfills are available for decomposing the MSW. However, the conventional bioreactor landfills suffer different environmental problems associated with the installation and functioning of MSW landfills such as slow rate of decomposition of the MSW, emission of gaseous pollutants, soil contamination, and water or air pollution.

The above information is presented as background information only to help the reader to understand the present invention. Applicants have made no determination and make no assertion as to whether any of the above might be applicable as Prior Art with regard to the present application.

SUMMARY

Accordingly the embodiments herein provide a system for decomposing municipal solid waste (MSW) under anaerobic conditions. The system includes a bioreactor landfill with the MSW, a leachate recirculation unit in connection with the bioreactor landfill, a multilevel thermocouple unit, placed inside the bioreactor landfill for monitoring temperature in the bioreactor landfill. Further, the system includes a sensor for monitoring moisture level within the bioreactor landfill. Furthermore, the leachate recirculation unit is configured to initiate recirculation of a leachate, collected from the bioreactor landfill, when temperature in the bioreactor reaches a determined temperature and a determined moisture level.

Accordingly the embodiments herein provide a method for method for decomposing municipal solid waste (MSW) under anaerobic conditions. The method includes monitoring, by a multilevel thermocouple unit, temperature in a bioreactor landfill. Further, the method includes monitoring, by a sensor, moisture level within the bioreactor landfill. Furthermore, the method includes initiating, by the leachate recirculation unit, recirculation of a leachate collected from the bioreactor landfill, when temperature in the bioreactor reaches a determined temperature and a determined moisture level.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This invention is illustrated in the accompanying drawings, throughout which like reference letters indicate corresponding parts in the various figures. The embodiments herein will be better understood from the following description with reference to the drawings, in which.

DETAILED DESCRIPTION

Figure 1:
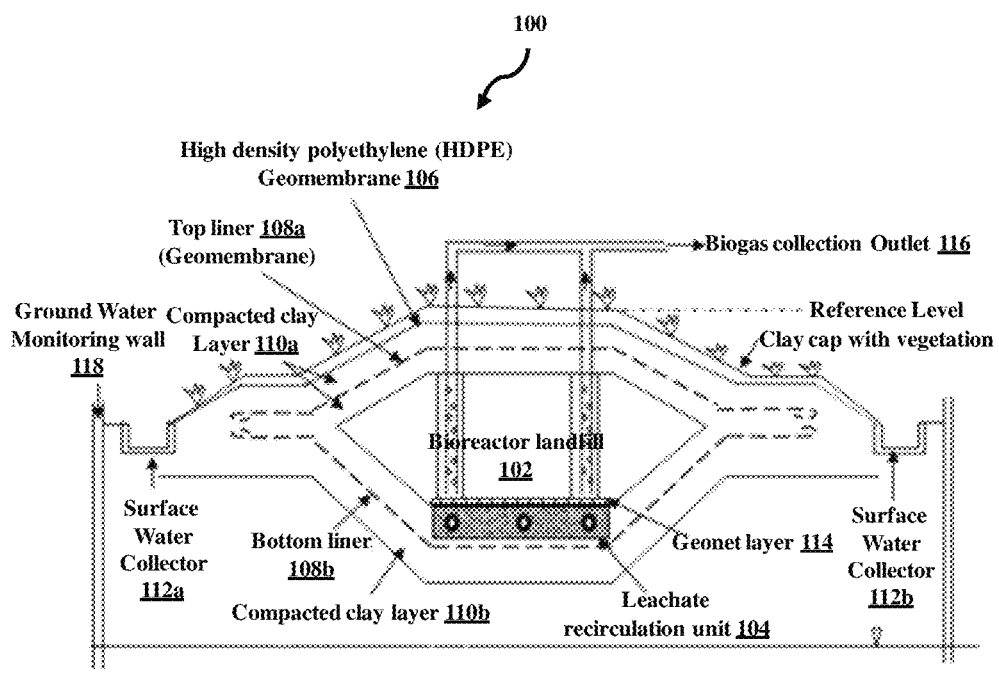
FIG. 1 illustrates a system for decomposing municipal solid waste (MSW), according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

The embodiments herein achieve a system and method for decomposing municipal solid waste (MSW) under anaerobic conditions. The system includes a bioreactor landfill with the MSW, a leachate recirculation unit in connection with the bioreactor landfill, a multilevel thermocouple unit, placed inside the bioreactor landfill for monitoring temperature in the bioreactor landfill. Further, the system includes a sensor for monitoring moisture level within the bioreactor landfill. Furthermore, the leachate recirculation unit is configured to initiate recirculation of a leachate, collected from the bioreactor landfill, when temperature in the bioreactor reaches a determined temperature and a determined moisture level.

In an embodiment, the leachate recirculation unit includes a storage unit which is placed external to the bioreactor landfill for storing the leachate collected from the bioreactor landfill. Further, the leachate recirculation unit includes a pump to recirculate the collected leachate into the bioreactor landfill.

In an embodiment, the leachate recirculation unit frequently obtains values corresponding to the temperature and moisture level of the MSW in the bioreactor landfill.

In an embodiment, the determined temperature corresponds to an increase in temperature of the MSW and the determined moisture level corresponds to a decrease in moisture level in the MSW.

Unlike the conventional bioreactor landfills, the proposed bioreactor landfill can be used to efficiently recirculate the leachate to the bioreactor landfill, thus eliminating the leakage of the leachate into the ground. The proposed bioreactor landfill employs a closed loop system in which the temperature and moisture level inside the bioreactor landfill are monitored for recirculating the leachate back to the bioreactor landfill. The proposed bioreactor landfill can be used by a small community (i.e., with a population of 25000). It should be noted that the proposed bioreactor landfill can be effective with the usage instrumentation namely sensor (for example: Frequency Domain Reflectometry (FDR) and multilevel thermocouples) for monitoring the moisture content and temperature respectively. Further, the proposed bioreactor landfill maintains favourable conditions for bacterial activity, which can accelerate the decomposition rate by controlling the moisture level and temperature of the MSW by scheduling leachate recirculation. The proposed bioreactor landfill can be used to ascertain the emission of biogas due to decomposition of MSW.

Referring now to the drawings and more particularly to FIGS. 1 through 7 where similar reference characters denote corresponding features consistently throughout the figures, there are shown preferred embodiments.

FIG. 1 illustrates a system 100 for decomposing municipal solid waste (MSW) under anaerobic conditions, according to embodiments as disclosed herein. As depicted in the FIG. 1, the system 100 includes a bioreactor landfill 102, a leachate recirculation unit 104, a high density polyethylene (HDPE) geomembrane 106, a top liner 108a, a bottom liner 108b, compacted clay layers (110a and 110b), surface water collectors (112a and 112b), a geonet layer 114, a biogas collection outlet 116 and a ground water monitoring wall 118.

The bioreactor landfill 102 is designed in a hexagonal shape as shown in the FIG. 1. The bioreactor landfill 102 is filled with the MSW. In an example, the height of the bioreactor landfill 102 is 1.5 meter and the length is 4.5 meter. Further, the width of the bioreactor landfill 102 is 3.5 meter (marked as reference level in the FIG. 1). The bioreactor landfill 102 is surrounded by the top liner 108a, the bottom liner 108b and the compacted clay layers 110a and 110b.

The bottom liner 108b separates and prevents the MSW from the underlying and surrounding natural soil or ground water. The bottom liner 108b separates and prevents the MSW from the underlying and surrounding natural soil or ground water by providing appropriate sealing layers at the base and side of the bioreactor landfill 102 by a combination of compacted clay soil with geomembrane. The HDPE geomembrane 106 with a protection cover is provided to the bioreactor landfill 102. In an example, the thickness of the HDPE geomembrane 106 is 1.5 mm with the protection cover of 500 mm.

Below the bottom liner 108b (geomembrane), the compacted clay layer 110b is provided with a permeability less than $1 \times 10^{-7}$ cm/sec (natural soil modified with additives such as bentonite to reach the desired level of permeability), supported by 200 mm subgrade layer is used.

The leachate recirculation unit 104 is provided to collect the leachate under gravity using perforated HDPE pipes placed in the bioreactor landfill. The leachate recirculation unit 104 can be configured to recirculate the leachate into the bioreactor landfill 102. In an embodiment, the leachate recirculation unit 104 includes a leachate collection pipe, a storage unit, a pump and a leachate recirculation pipe. The one or more actions performed by the leachate recirculation unit 104 are explained in conjunction with FIG. 2.

In an embodiment, the leachate recirculation unit 104 frequently obtains values corresponding to the temperature and moisture level of the MSW in the bioreactor landfill 102.

The top liner 108a (with clay cover and vegetation as depicted in the FIG. 1) is provided to avoid the infiltration of runoff water into the bioreactor landfill 102 and exit of biogases into the atmosphere. In an example, the top liner 108a consists of 450 mm thick soil layer with vegetation, the geonet layer 114 for drainage of water to side drains, 1.5 mm thick geomembrane layer and 600 mm thick barrier layer of local clay soil.

The surface water collectors 112a and 112b is designed around the bioreactor landfill 102 (as shown in the FIG. 1) to restrict the quantity of water entering into the bioreactor landfill 102, for minimizing the generation of leachate and to prevent the pollution of surface water sources. In an example, the surface water collector is designed for a rainfall intensity of 500 mm/hr.

The biogas collection outlet 116 consists of a series perforated pipes (for example, each pipe has 100 mm diameter) embedded in the bioreactor landfill 102. The series of perforated pipes is surrounded with bentonite plug and solid casing at the top and a thick gravel packing in the remaining portion, for venting biogas into the pipes from the solid waste. The biogas collected through the biogas collection outlet 116 (from the bioreactor landfill 102) can be stored in a separate gas holding tank.

The ground water monitoring wall 118 is provided for monitoring leachate migration into the subsoil and surrounding soil. The HDPE perforated pipes (for example, with 110 mm diameter) are installed in the soil at 5 m distance from the edge of bioreactor landfill 102, one at upstream and another at downstream of the bioreactor landfill 102. The quality of the water collected from HDPE pipes can be analyzed to assess the extent of leachate migration.

The FIG. 1 shows a limited overview of the system 100 but, it is to be understood that other embodiments are not limited thereto. The labels or names in the FIG. 1 are used only for illustrative purpose and does not limit the scope of the invention. Further, the system 100 can include any number of units or sub-units communicating among each other along with the other components. Likewise, the functionalities of each unit can be combined by a single unit or can be distributed among each other in a manner different than described herein without departing from the scope of the embodiments.

Figure 2:
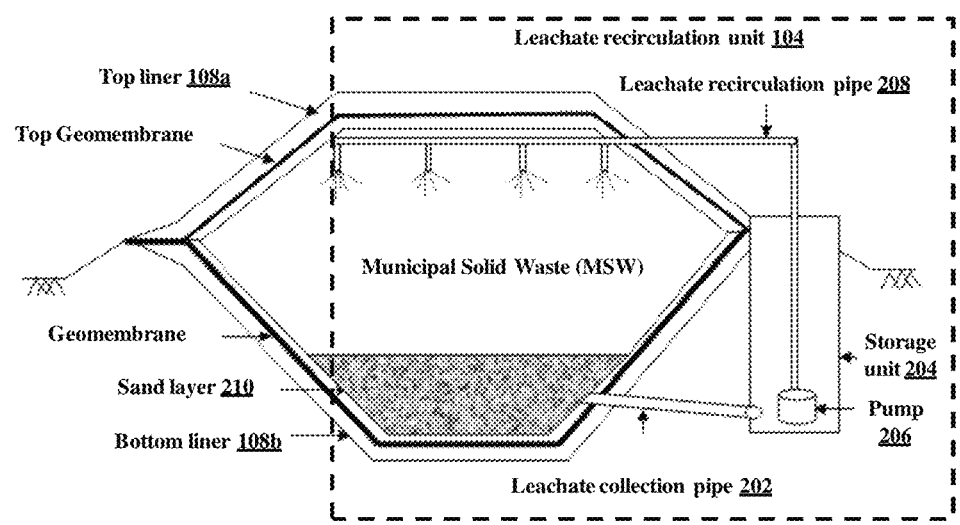
FIG. 2 illustrates a leachate recirculation unit of the system described in the FIG. 1, according to the embodiments as disclosed herein.

FIG. 2 illustrates a leachate recirculation unit 104 of the system 100 described in the FIG. 1, according to the embodiments as disclosed herein. As depicted in the FIG. 2, the leachate recirculation unit 104 includes a leachate collection pipe 202, a storage unit 204, a pump 206 and a leachate recirculation pipe 208. The leachate collection pipe 202 is connected to the storage unit 204 which is placed external to the bioreactor landfill 102. The storage unit 204 stores the leachate from the bioreactor landfill 102 through the leachate collection pipe 202. The leachate stored in the storage unit 204 is recirculated into the bioreactor landfill 102 by employing the pump 206. The pump 206 recirculates the leachate into the bioreactor landfill through the leachate recirculation pipe. In an embodiment, the leachate recirculation unit 104 frequently obtains values corresponding to the temperature and moisture level of the MSW in the bioreactor landfill 102.

In an embodiment, the leachate recirculation unit 104 can be configured to initiate recirculation, of the leachate collected from the bioreactor landfill 102 when temperature in the bioreactor reaches the determined temperature and the determined moisture level. In an embodiment, the determined temperature corresponds to an increase in temperature of the MSW and the determined moisture level corresponds to the decrease in moisture level in the MSW.

The maximum leachate head on the liner is maintained at 0.3 meter. The leachate recirculation unit 104 consists of a thick drainage layer of coarse sand and gravel with permeability higher than $1 \times 10^{-2}$ cm/sec (MSW Rule, 2000), and two sloping HDPE perforated pipes having 90 mm diameter connected to a single 110 mm HDPE pipe, for the collection of leachate in the storage unit 204.

In an embodiment, size of the storage unit 204 is decided based on estimated quantity of the leachate generation and In an example, depth of the storage unit 204 is kept two meters below the reference level and the capacity of the pump 206 is chosen as two horse power (2 HP). The pump 206 is placed in the storage unit 204 and is connected to the leachate recirculation pipes 208 (made of the HDPE for example, with a diameter of 40 mm diameter, inserted in the MSW, as shown in the FIG. 2.

Figure 3:
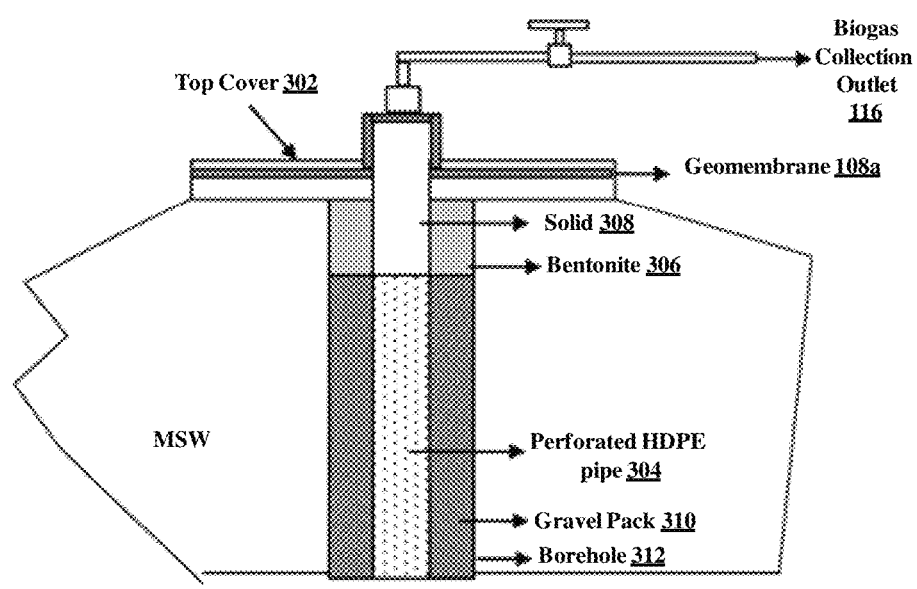
FIG. 3 illustrates a schematic of a biogas collection system, according to the embodiments as disclosed herein.

FIG. 3 illustrates a schematic of a biogas collection system, according to the embodiments as disclosed herein. As depicted in the FIG. 3, the system 100 includes a top cover 302, a perforated HDPE pipe 304, a bentonite plug 306, a solid casing 308, gravel pack 310 and a borehole 312.

The system 100 includes a series perforated HDPE pipes 304 (for example, each pipe has 100 mm diameter) embedded in the bioreactor landfill 102. The series of perforated HDFE pipes 304 is surrounded with the bentonite plug 306 and the solid casing 308 at the top and the thick gravel pack 310 in the remaining portion, for venting biogas into the pipes from the solid waste. The biogas collected through the biogas collection outlet 116 can be stored in a separate gas holding tank.

Figure 4:
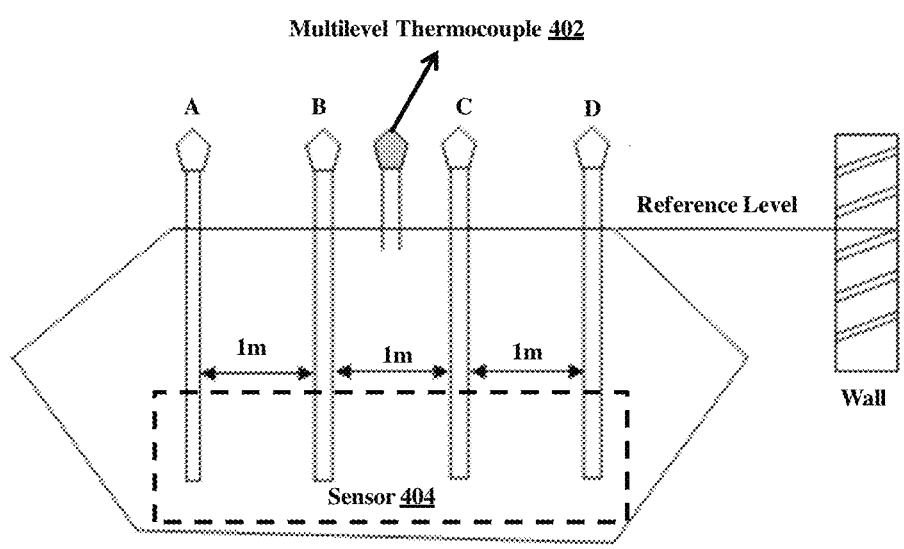
FIG. 4 shows access tubes of a sensor and a multilevel thermocouple installed in the system as described in FIG. 1, according to the embodiments as disclosed herein.

FIG. 4 illustrates a multilevel thermocouple and access tubes of a sensor 404 installed in the system 100, according to the embodiments as disclosed herein. In an embodiment, a multilevel thermocouple 402 and the sensor 404 is installed in the system 100 for monitoring the temperature and the moisture level within the bioreactor landfill 102 respectively. In an example, the sensor 404 can be a frequency domain reflectometry (FDR) probe which can be installed in the system 100 for monitoring the moisture level. As depicted in the FIG. 4, four FDR probes A, B, C and D are installed in the system 100 for monitoring the moisture level within the bioreactor landfill 102. Although the sensor 404 is mentioned as the FDR probe, any other sensor can be used for measuring or monitoring the moisture level in the bioreactor landfill 102.

In an embodiment, monitoring of the ambient temperature and humidity can be performed by employing e a temperature and humidity meter (designated as TH meter). The calibration of the temperature and humidity meter can be carried out with the help of an 'environment chamber' by operating it at 270 C. and 60% relative humidity and the TH meter values are found to be 27±0.50 C. and 60±1%, respectively. Further, the multilevel thermocouple and the FDR probes are employed for monitoring of temperature and moisture level of the MSW in the bioreactor landfill as discussed herein.

The multilevel thermocouple is installed in the central access tube, shown with the reference numeral 402 in the FIG. 4. In an embodiment, the multilevel thermocouple can be connected to a data logger for continuous monitoring of temperature at different depths (such as for example at 0.3, 0.5 and 0.7 m) from reference level.

In an embodiment, the multilevel thermocouple can be connected to the data logger for recording the temperature over a period of time. In an example, calibration of the thermocouple can be performed with the help of hot water and ice cubes and the results were found to vary by less than 1° C.

The FDR works on 'frequency domain reflectometery' technique or the capacitance technique of determination of volumetric moisture level. This technique employs a split cylindrical electrode probe that can be moved in a PVC access tube, which is inserted in the soil mass. It houses a metallic capacitor, which is connected to an oscillator, to form an electrical circuit, and the change in the operating frequency of the circuit enables detection of the changes in the soil moisture. The frequency, at which the amplitude is maximum, can be related to the water content of the soil mass in which the FDR probe is inserted.

The calibration of the FDR probe consists of three steps: (a) recording the observations in the air, by placing the FDR probe inserted in the access tube in air for 10 seconds, which is designated as the air count, RA, and represents possible dry state of the soil, (b) recording the observations in water bath, by placing the FDR probe inserted in the access tube in water for 10 seconds, which is designated as the water count, RW, and represents fully saturated state of the soil and (c) recording the observations, by placing the FDR probe inserted in the access tube, in the MSW, for 10 seconds, which is designated as the field count, RF. Further, the display unit shows scaled frequency, SF, values which is computed for the MSW, using the equation 1 as given below.

$$SF = R_A - R_F / R_A - R_W \qquad (1)$$

The procedure for recording RF in the MSW is as described herein. As depicted in the FIG. 4, four access tubes, designated as A, B, C and D (made of PVC, having 50 mm internal diameter, 3 mm wall thickness and 1.5 m long) are inserted from the top of the bioreactor landfill 102, at a center-to-center spacing of 1 m.

In an embodiment, boreholes are created with the help of manual auger (for example with a diameter of a 56 mm diameter) for easy insertion of the access tubes. The samples of MSW are collected from the boreholes corresponding to 0.3, 0.5 and 0.7 meter depths and the gravimetric moisture level is determined for the samples. Subsequently, properly shredded MSW is inserted into the boreholes before the installation of the access tubes. This helps in filling of the gaps between the tube and the surrounding MSW material. After inserting access tubes, expandable rubber bungs are placed from inside at the bottom of tubes to avoid entry of surrounding leachate into the access tubes A, B, C and D.

The recording of moisture content (in terms of SF) and temperature in bioreactor landfill was done on a daily basis by inserting the FDR probe and the thermocouple in the access tubes provided for the same. After the measurement of temperature and moisture level, both the FDR probe and the multilevel thermocouple can be removed and stored in a controlled environment and the access tubes can be closed with top caps, to prevent loss of generated biogas during the decomposition process or direct ingress of water from outside to the bioreactor landfill 102.

Figure 5:
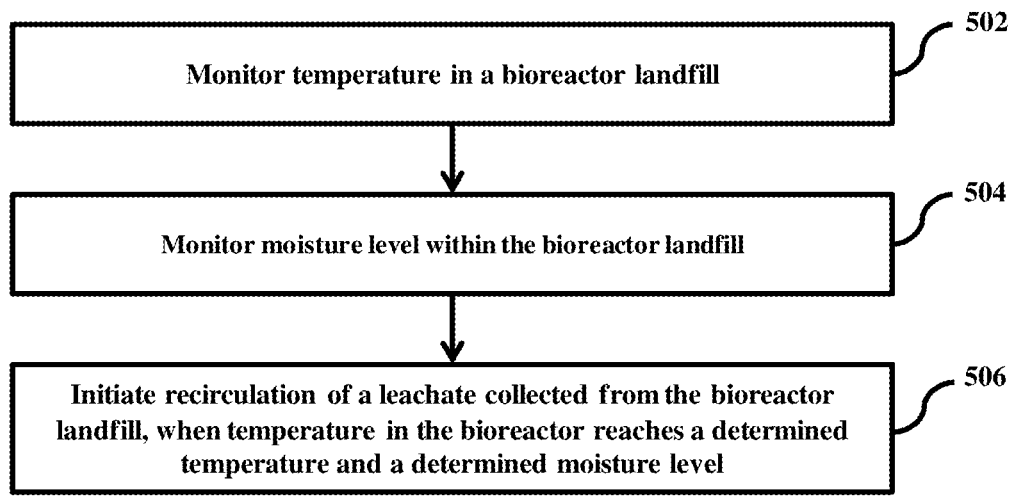
FIG. 5 is a flow chart illustrating a method for decomposing the MSW under anaerobic conditions, according to the embodiments as disclosed herein.

FIG. 5 is a flow chart illustrating a method for decomposing the MSW under anaerobic conditions, according to the embodiments as disclosed herein. At step 502, the method 500 includes monitoring the temperature in the bioreactor landfill 102. The method 300 allows multilevel thermocouple 402 to monitor the temperature in the bioreactor landfill 102. In an example, the multilevel thermocouple 402 is placed in the central access tube. In an embodiment, the multilevel thermocouple can be connected to the data logger for continuous monitoring of temperature at different depths (such as for example at 0.3, 0.5 and 0.7 meter) from the reference level.

At step 504, the method 500 includes monitoring the moisture level in the bioreactor landfill 102. The method 500 allows the sensor to monitor the moisture level in the bioreactor landfill 102. In an example, the sensor can be the FDR probe which can be installed in the system 100 for monitoring the moisture level. The four FDR probes namely A, B, C and D are installed in the system 100 for monitoring the moisture level within the bioreactor landfill 102.

At step 506, the method 500 includes initiating recirculation of a leachate collected from the bioreactor landfill, when temperature in the bioreactor reaches the determined temperature and the determined moisture level. The method 500 allows the leachate recirculation unit 104 to initiate recirculation of a leachate collected from the bioreactor landfill, when temperature in the bioreactor reaches a determined temperature and a determined moisture level. In an embodiment, the leachate recirculation unit 104 frequently obtains values corresponding to the temperature and moisture level of the MSW in said bioreactor landfill 102.

In an embodiment, the determined temperature corresponds to an increase in temperature of the MSW and the determined moisture level corresponds to a decrease in moisture level in the MSW.

The various actions, acts, blocks, steps, or the like in the method 500 may be performed in the order presented, in a different order or simultaneously. Further, in some embodiments, some of the actions, acts, blocks, steps, or the like may be omitted, added, modified, skipped, or the like without departing from the scope of the invention.

Figure 6:
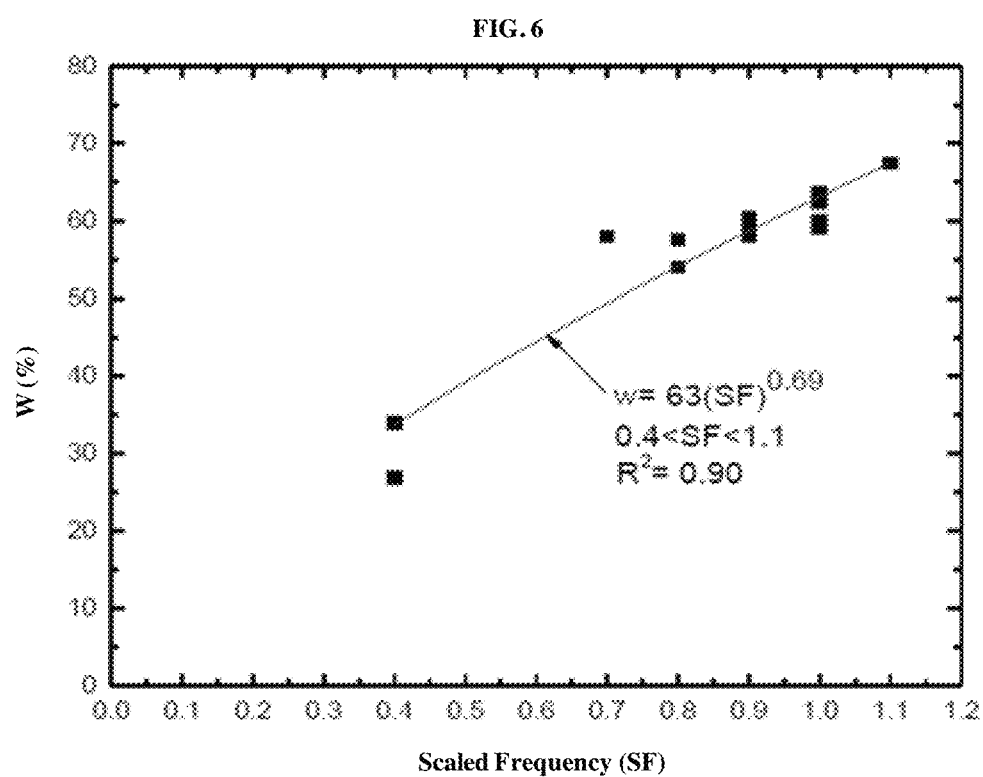
FIG. 6 is graph showing variation of a scaled frequency with moisture level, according to the embodiments as disclosed herein.

FIG. 6 is graph showing variation of a scaled frequency (SF) with moisture level, according to the embodiments as disclosed herein.

After installation of all the four access tubes and subsequently inserting the FDR probes A, B, C and D in the access tubes, scaled frequency, SF, is measured at different depths in these four access tubes. Usually SF is plotted against the volumetric moisture content, which can be defined by equation (2)

$$SF = A \cdot \theta^B + C \quad (2)$$

$$\text{where } \theta = (\gamma_d/\gamma_w) \cdot w \quad (3)$$

where A, B and C are empirical constants, d is the dry unit weight of the material (in kg/m3), w is the unit weight of water (in kg/m3), and w is the gravimetric moisture content.

Due to high heterogeneity of the MSW, its density, γ will vary at different locations. However, the density cannot be measured due to the reasons beyond control at several locations and hence the average density of the MSW is computed to be equal to 481 kg/m3. The SF has been related to the gravimetric moisture content, w, as depicted in the FIG. 6. The relationship between the w and SF can be mathematically expressed by the equation (4) as given below.

$$w = A \cdot SF^B \quad (4)$$

Where, SF=scaled frequency and the SF varies between 0.4 and 1.1, as shown in the FIG. 6. The values A and B are empirical coefficients and their values are obtained as 63 and 0.69, respectively. The equation (4) can be employed for obtaining the gravimetric moisture content from the corresponding SF values, for day-to-day monitoring of the moisture level in the bioreactor landfill 102.

Figure 7:
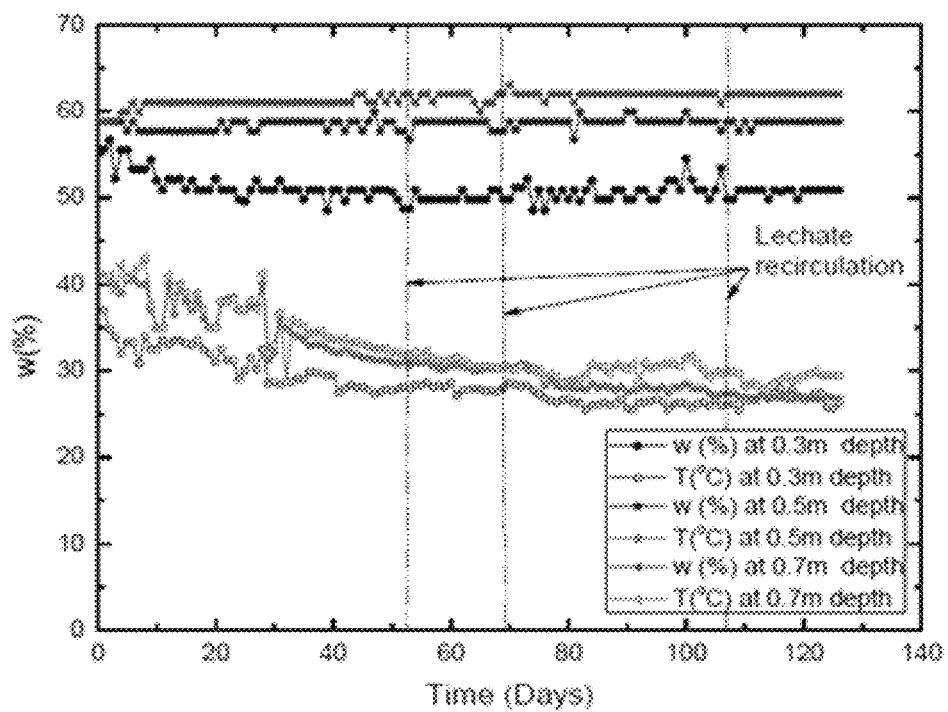
FIG. 7 is a graph showing variation of moisture level and temperature with time, according to the embodiments as disclosed herein.

FIG. 7 is a graph showing variation of moisture level and temperature with time, according to the embodiments as disclosed herein. The moisture level w and the temperature T of the MSW in the bioreactor landfill 102 are monitored over a period of time using the sensor (FDR probe) and the multilevel thermocouple respectively and the variation of the w and T with time, corresponding to 0.3, 0.5 and 0.7 meter depths from the level as shown in the FIG. 7.

From the FIG. 7, it can be inferred, that there is a reduction of moisture level during the decomposition process corresponding to 0.3 meter depth. It should be noted, that there is a release of heat energy during the decomposition of MSW due to bacterial (metabolism) activity, which results in an increase of temperature of the MSW and hence a decrease in the moisture level. This can be substantiated from the temperature variation in the FIG. 7, where the turbulence in the temperature, especially in the initial 30 days (when decomposition of food and vegetable waste, which constitutes significant quantity of the total waste takes place), indicates the increase in bacterial activity within the system 100. However, at depths of 0.5 and 0.7 meter, similar conclusion cannot be derived, as the leachate in the MSW will slowly infiltrate downwards, due to gravity, over a period of time, which in turn will increase the moisture level of the material placed below. Hence, the lower portion of the landfill becomes saturated (as it is just above the leachate collection layer), which can be confirmed from increasing moisture content at 0.7 meter depth, initially, which subsequently becomes steady.

It should be noted that almost 65-70% of the total waste (most of the organic waste excluding plastic) would have completed decomposition in about 75 days, which may be achieved by controlling moisture content and temperature of the MSW (through recirculation of leachate), by employing FDR probe and thermocouple, respectively. Incidentally, from FIG. 7, it can be observed, that the moisture level and temperature is almost constant by this period.

Further, it should be noted that, the initial moisture level of the MSW varies between 55-60%, which is within the optimum range of 40-65%, for fast decomposition of the MSW. Further, when the moisture content of the MSW drops to 50%, due to drainage of the leachate, consumption of moisture during bacterial activity and minor evaporation losses from the gas collection pipes, especially in top portion of SEBL; efforts were made to maintain the moisture content in optimum range, by recirculation of the leachate collected from the SEBL in the sump well and by using additional makeup water. The leachate collected was recirculated with additional makeup water of 100 L after 53 days, 69 days and 107 days, when drop in the moisture content is observed as shown in the FIG. 7. It should be noted that the recirculation is been carried to maintain moisture content of MSW above 50%, especially in top portion of SEBL. The leachate generated during the same period has been found to be 40 Liter, 60 Liter and 44 Liter, respectively.

The embodiments disclosed herein can be implemented through at least one software program running on at least one hardware device to control the elements.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. A system for decomposing municipal solid waste (MSW) under anaerobic conditions, the system comprising:
    a bioreactor landfill with said MSW;
    a leachate recirculation unit in connection with said bioreactor landfill;
    at least one access tube placed inside said bioreactor landfill,
        wherein said at least one access tube encloses a multilevel thermocouple unit for monitoring temperature of said MSW at different depth levels in said bioreactor landfill, and
        wherein said at least one access tube encloses a sensor for monitoring moisture level of said MSW in said bioreactor landfill; and
    wherein said leachate recirculation unit is configured to initiate recirculation of a leachate collected from said bioreactor landfill when said temperature of said MSW in said bioreactor landfill and said moisture level of said MSW within said bioreactor landfill reaches a determined temperature and a determined moisture level.

2. The system of claim 1, wherein said leachate recirculation unit includes a storage unit, placed external to said bioreactor landfill, to store said leachate collected from said bioreactor landfill, and a pump to recirculate said collected leachate into said bioreactor landfill.

3. The system of claim 1, wherein said leachate recirculation unit, in connection with said multilevel thermocouple unit and said sensor, frequently obtains values corresponding to said temperature and said moisture level of said MSW in said bioreactor landfill.

4. The system of claim 1, wherein said determined temperature corresponds to an increase in temperature of said MSW.

5. The system of claim 1, wherein said determined moisture level corresponds to a decrease in said moisture level of said MSW.

6. A method for decomposing municipal solid waste (MSW) under anaerobic conditions, the method comprising:
    monitoring, by a multilevel thermocouple unit placed inside at least one access tube, temperature of said MSW at different depth levels in a bioreactor landfill;
    monitoring, by a sensor placed inside said at least one access tube, moisture level of said MSW within said bioreactor landfill; and
    initiating, by a leachate recirculation unit, recirculation of a leachate collected from said bioreactor landfill when said temperature of said MSW in said bioreactor landfill and said moisture level of said MSW within said bioreactor landfill reaches a determined temperature and a determined moisture level.

7. The method of claim 6, wherein said multilevel thermocouple unit and said sensor, frequently obtains values corresponding to said temperature and said moisture level of said MSW in said bioreactor landfill.

8. The method of claim 6, wherein said determined temperature corresponds to an increase in temperature of said MSW.

9. The method of claim 6, wherein said determined moisture corresponds to a decrease in said moisture level of said MSW.

* * * * *